US011903727B2

(12) United States Patent
Kelly et al.

(10) Patent No.: US 11,903,727 B2
(45) Date of Patent: Feb. 20, 2024

(54) METHOD AND DEVICE FOR HEALTH DEVICES AND WEARABLE/IMPLANTABLE DEVICES

(71) Applicant: KONINKLIJKE PHILIPS N.V., Eindhoven (NL)

(72) Inventors: Declan Patrick Kelly, Shanghai (CN); Michael Martin Scheja, Shanghai (CN); Wei Chen, Eindhoven (NL); Rim Helaoui, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 332 days.

(21) Appl. No.: 16/312,373

(22) PCT Filed: Jun. 22, 2017

(86) PCT No.: PCT/EP2017/065328
§ 371 (c)(1),
(2) Date: Dec. 21, 2018

(87) PCT Pub. No.: WO2018/001840
PCT Pub. Date: Jan. 4, 2018

(65) Prior Publication Data
US 2019/0223787 A1  Jul. 25, 2019

(30) Foreign Application Priority Data

Jun. 29, 2016 (WO) ................ PCT/CN2016/087725
Aug. 1, 2016 (EP) ..................................... 16182183

(51) Int. Cl.
*A61B 5/00* (2006.01)
*A61B 5/0205* (2006.01)
(Continued)

(52) U.S. Cl.
CPC .......... *A61B 5/4848* (2013.01); *A61B 5/0002* (2013.01); *A61B 5/0024* (2013.01);
(Continued)

(58) Field of Classification Search
CPC ................ A61B 5/4848; A61B 5/0024; A61B 2560/0209
See application file for complete search history.

(56) References Cited

U.S. PATENT DOCUMENTS 9,393,460 B1 * 7/2016 Emigh ................... A61B 5/103
2009/0030285 A1 * 1/2009 Andersen ................ A61B 7/04
600/300

(Continued)

FOREIGN PATENT DOCUMENTS

WO  2010018518 A1  2/2010
WO  2011083377 A1  7/2011
(Continued)

OTHER PUBLICATIONS

Semeco, Arlene "The Top 10 Benefits of Regular Exercise", Healthline.*
(Continued)

*Primary Examiner* — Lynsey C Eiseman

(57) ABSTRACT

A method for power management of a wearable device or an implantable device comprising a sensor, the sensor configured for providing a physiological information of a user, the sensor being further configured to be operated in at least two power modes comprising a first power mode and a second power mode, wherein in the first power mode the physiological information of the user is gathered and in the second power mode the sensor consumes less power than in the first power mode, the method comprising: receiving a signal being indicative of whether a health device which is configured to treat a health condition of the user is in use, wherein the health device is positioned at a different location (Continued)

with respect to the user than the wearable device or the implantable device; and based on the signal operating the sensor for a time duration in the first power mode; and operating the sensor in the second power mode thereafter.

17 Claims, 5 Drawing Sheets

(51) Int. Cl.
    *A61B 5/08*      (2006.01)
    *A61B 5/1455*   (2006.01)
    *A61B 5/024*    (2006.01)
    *A61B 5/0215*   (2006.01)

(52) U.S. Cl.
    CPC .......... *A61B 5/0205* (2013.01); *A61B 5/4839* (2013.01); *A61B 5/681* (2013.01); *A61B 5/686* (2013.01); *A61B 5/024* (2013.01); *A61B 5/0215* (2013.01); *A61B 5/02055* (2013.01); *A61B 5/02438* (2013.01); *A61B 5/0816* (2013.01); *A61B 5/14551* (2013.01); *A61B 5/6898* (2013.01); *A61B 2560/0209* (2013.01)

(56) References Cited

U.S. PATENT DOCUMENTS

| | | | |
|---|---|---|---|
| 2013/0027186 A1* | 1/2013 | Cinbis | A61B 5/0028 340/10.1 |
| 2014/0197947 A1* | 7/2014 | Bahorich | G16H 40/67 340/539.12 |
| 2015/0012068 A1 | 1/2015 | Bradley et al. | |
| 2015/0057967 A1 | 2/2015 | Albinali | |
| 2015/0173617 A1 | 6/2015 | Sheynblat et al. | |
| 2015/0173631 A1 | 6/2015 | Richards et al. | |
| 2015/0182160 A1 | 7/2015 | Kim et al. | |
| 2015/0190078 A1 | 7/2015 | Lisogurski | |
| 2015/0335295 A1 | 11/2015 | Park et al. | |
| 2016/0026212 A1* | 1/2016 | Lee | G06F 1/3231 361/679.03 |
| 2016/0317067 A1* | 11/2016 | Lee | A61B 5/1118 |
| 2017/0014068 A1* | 1/2017 | Gotoh | A61B 5/1118 |

FOREIGN PATENT DOCUMENTS

| | | |
|---|---|---|
| WO | 2014027273 A1 | 2/2014 |
| WO | 2016111633 A1 | 7/2016 |

OTHER PUBLICATIONS

RF Wirless World "Types of Medical sensors/ Functions of medical sensors".*
Global Spec "Light Guides Information".*
Nakamura et al : "Collaborative Processing of Wearable and Ambient Sensor System for Blood Pressure Monitoring"; Sensors 2011, 11, pp. 6760-6770.

* cited by examiner

Table 1

| Device | Name of sensor | Physiological parameter | Duration | Sampling rate |
|---|---|---|---|---|
| Inhaler | Heart rate sensor | Heart rate | 10 mins | High |
| Inhaler | Breathing rate sensor | Breathing rate | 10 mins | High |
| Inhaler | SpO2 sensor | Blood oxygen saturation | 10 mins | High |
| Phototherapy device for treating pain | Heart rate sensor | Heart rate variability (HRV) for stress determination | 15 mins | Low |
| CPAP device | Breathing rate sensor | Breathing rate | 30 mins | Low |

FIG. 2

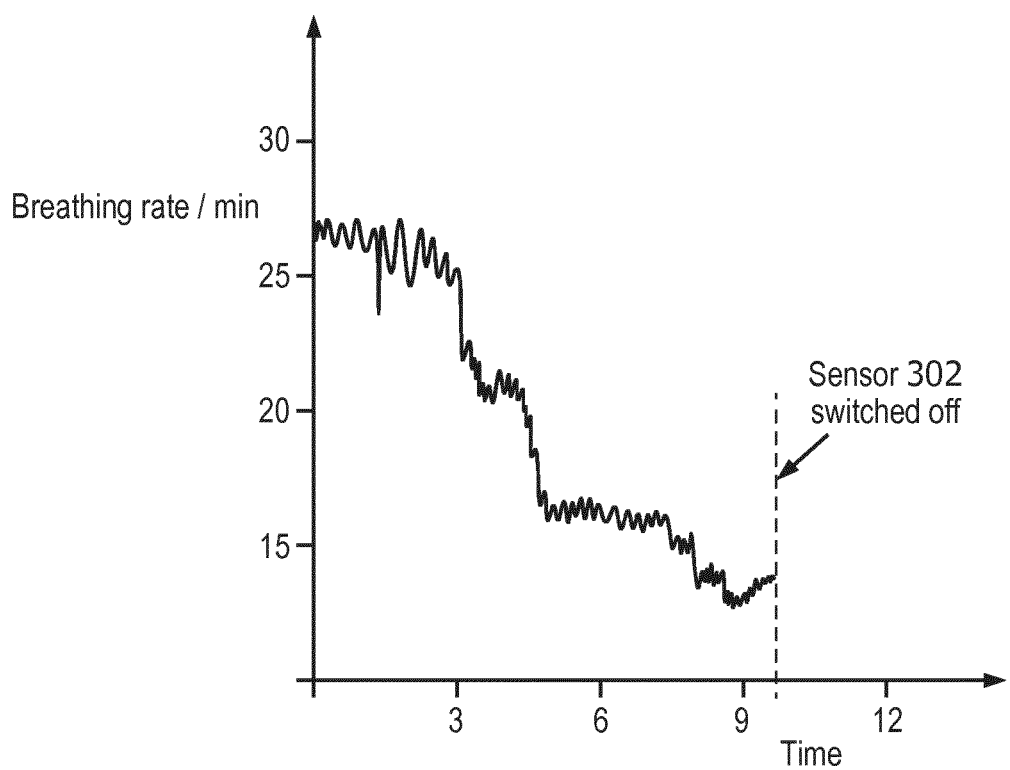

FIG. 3

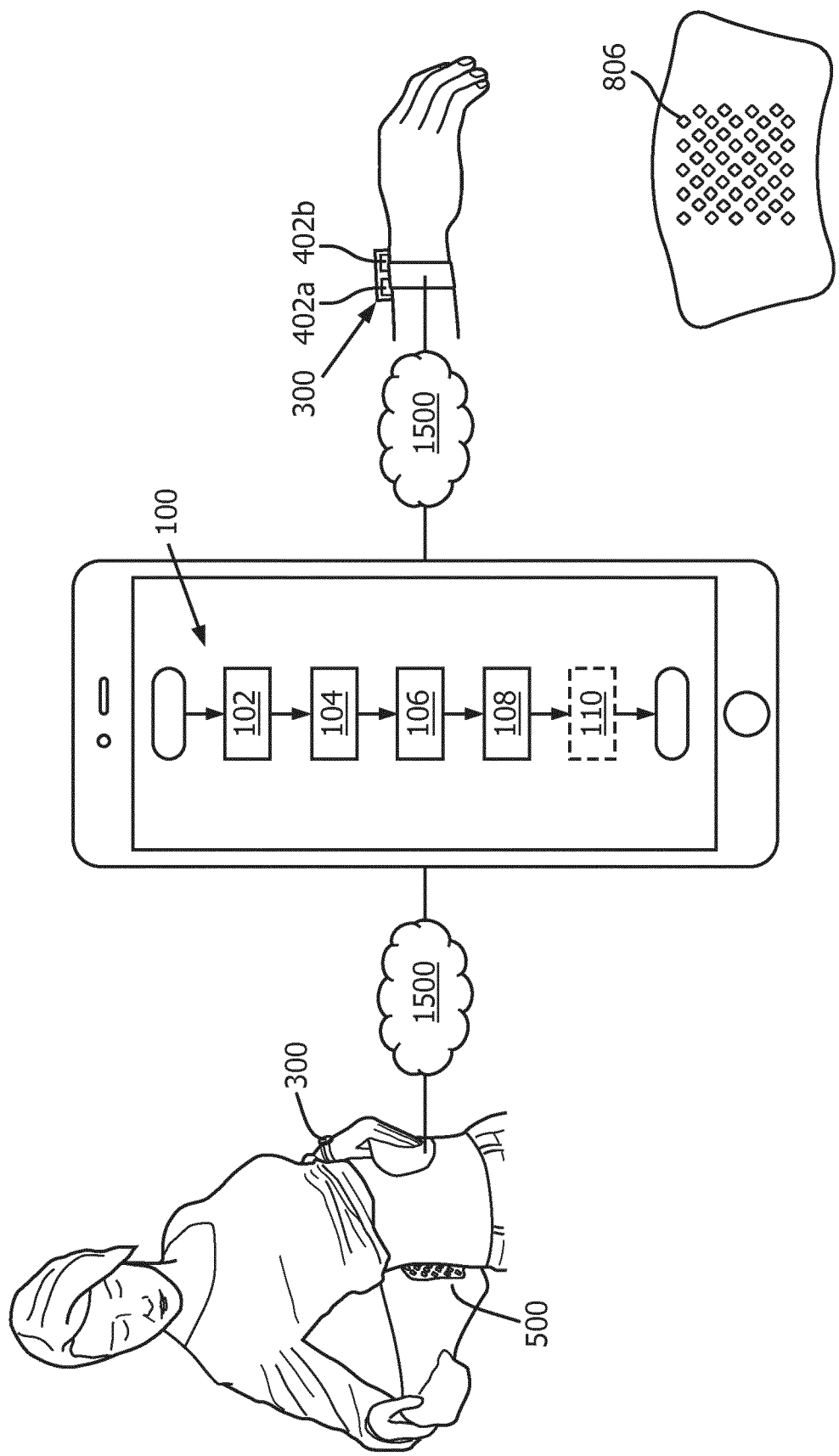

METHOD AND DEVICE FOR HEALTH DEVICES AND WEARABLE/IMPLANTABLE DEVICES

CROSS-REFERENCE TO RELATED APPLICATIONS

This patent application claims the priority benefit under 35 U.S.C. § 371 of international patent application no. PCT/EP2017/065328, filed Jun. 22, 2017, which claims the priority benefit of European patent Application No. 16182183.0, filed Aug. 1, 2016, and PCT patent Application No. PCT/CN2016/087725, filed Jun. 29, 2016, the contents of which are hereby incorporated by reference herein.

FIELD OF THE INVENTION

The present invention relates to connected health devices and a computer implemented method controlling the connected devices and wearable devices. More specifically, the present invention relates to power management of a wearable device or an implantable device that is configured to provide at least one physiological information comprising vital sign information.

BACKGROUND OF THE INVENTION

There are different kinds of health devices available in the market, such as asthma inhalers, pain relieving devices, sleep therapy devices, etc. These are further enabled with wireless connectivity. The current purpose of these connected health devices is to transfer treatment duration and date on which the treatment was performed, etc. at a remote server, or to a mobile device of a user. The current purpose of the data transfer is merely to maintain a log of treatment.

Recently, a second set of devices, popularly known a health/fitness trackers are catching popularity with people. These devices also monitor a variety of vital signs, such as heart rate, breathing rate, etc. However, these devices currently face a lot of challenges in terms of power management. Though, these devices utilize duty cycles, sampling rate of sensors to manage power, these devices still suffer battery problems. It so happens that when the data is most importantly required, the fitness tracker is low on battery and more so often dead due to insufficient battery charge.

SUMMARY OF THE INVENTION

The invention is defined by the claims.

Therefore, it is an object of the present invention to provide a method, a device and a system to better manage the power of the wearable device or implantable device. By implementing the method/device as proposed by the claims, the wearable device or implantable device is activated only when required and hence ensures the availability of important physiological information, such as vital signs. The vital signs (often shortened to just vitals) are a group of the four to six most important signs, such as body temperature, blood pressure, heart rate, and breathing rate, that indicate the status of the body's vital (life-sustaining) functions. Physiological information may also include physiological state information, such as stress, which can be derived from the vital signs.

It also is envisaged that functionality of the asthma inhalers, oxygen concentrators for COPD patients, CPAP devices for sleep apnea or pain relieving devices cannot be integrated with a typical, wrist/chest worn devices due to space constraints/form factor and ease of use. Hence, adaptive selection of vital sign information based on the health device being employed by the user not only helps in power management of the wearable device but also helps in better utilization of the data provided by the health device and the wearable device. In essence, the treatment/health device and wearable device complement each other to achieve multiple advantages.

In a first aspect, a method for power management of a wearable device or an implantable device is provided. The wearable device or the implantable device includes a plurality of sensors, each sensor configured for providing a corresponding physiological information of a user, each sensor being further configured to be operated in at least two power modes comprising a first power mode and a second power mode, wherein in the first power mode the physiological information of the user is gathered and in the second power mode the sensor consumes less power than in the first power mode. The method includes:

receiving a signal being indicative of whether a health device which is configured to treat a health condition of the user is in use, wherein the health device is positioned at a different location with respect to the user than the wearable device or the implantable device, wherein the signal further comprises information about a type of the health device in use;

selecting at least one sensor from the plurality of the sensors of the wearable device based on the type of the health device in use;

operating the selected at least one sensor in the first power mode for a time duration and operating the selected at least one sensor in second power mode thereafter. The method may be implemented at least in part in software.

This is particularly advantageous as the wearable device typically includes a variety of sensors and hence adaptive selection of the sensors based on the type of the health device in use further helps in power management and availability of right data.

In a second aspect, a computer program product as per claim 8 is provided. The computer program product, such as random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), an electrically erasable programmable read-only memory (EEPROM), and another like memory device. The computer program product can also be an application (app), preferable downloadable via network, that can be installed on a computer/a wireless communication device/a portable electronic device.

In a third aspect, a device for power management of a wearable device or an implantable device is provided. The wearable device or the implantable device comprising a plurality of sensors, each sensor configured for providing a corresponding physiological information of a user, each sensor being further configured to be operated in at least two power modes comprising a first power mode and a second power mode, wherein in the first power mode the physiological information of the user is gathered and in the second power mode the sensor consumes less power than in the first power mode, the device includes:

a processing unit;

a receiving module, in electronic communication with the processing unit, configured to receive a signal being indicative of whether a health device which is configured to treat a health condition of the user is in use, wherein the signal further comprises information about a type of the health device in use, wherein the health device is positioned at a different location with respect to the user than the wearable device or the implantable device;

a selecting module, in electronic communication with the processing unit, configured to generate and transmit a selecting signal for selecting at least one sensor from the plurality of the sensors of the wearable device based on the type of the health device in use; and an operating module, in electronic communication with the processing unit, configured to transmit an operating signal for (i) operating the selected sensor for a time duration in the first power mode; and (ii) operating the sensor in the second power mode thereafter.

In a fourth aspect, a system as per the claim 15 is provided.

Preferred embodiments of the invention are defined in the dependent claims. It shall be understood that the claimed system, device, and computer program product can have similar and/or identical preferred embodiments as the claimed method and as defined in the dependent claims.

In a further embodiment, the time duration is based on one of a first time duration threshold or a measure of effectiveness of the treatment provided by the health device, wherein the measure of effectiveness is evaluated based on the physiological information provided by the selected sensor.

The first time duration can be pre-programmed/pre-determined, for instance, breathing rate typically subsides within 10 minutes when an asthma relieving device is in use and hence 10 minutes can be set as the first time duration.

The measure of the effectiveness is calculated by comparing the measured physiological information with a pre-determined effectiveness threshold. The pre-determined effectiveness threshold can be based on the type of health device. For instance in case of an inhaler/asthma relieving device, the measured breathing rate will be continuously compared with a pre-determined breathing rate threshold (pre-determined effectiveness threshold) and once the measured breathing rate matches the pre-determined breathing rate threshold, the sensor will be operated in the second power mode. Thus, in effect, the duration in which the physiological information reaches (matches) the pre-determined effectiveness threshold is the duration for which the selected sensor is operated in the first power mode.

Furthermore, the measured physiological information can be evaluated in combination with the duration of usage of the device. For instance, if the measured breathing rate in the first three minutes of use of the health device matches a pre-determined effectiveness threshold then it is indicative that the treatment is effective, thereafter the corresponding sensor can be operated in the second power mode. In this example, the pre-determined effectiveness threshold can be a range of breathing rate, such as 12-18 breaths per minute within 3 minutes of the usage of the device.

In a further embodiment, the method further records the physiological information during the time duration. It is in particular advantageous as physiological information during the treatment is now stored and used for later use. For instance, the caregiver, either remotely or a doctor at a later time, can now understand/interpret the duration and physiological information data. For instance, the pain relieving device operated for 25 minutes, and it was recorded that stress gradually decreased during this time period. This gives clear indication on the effectiveness of the treatment. Also, this can help the caregiver to change the duration of the treatment duration.

In a further embodiment, operating the sensor in the second power mode comprises one of (i) deactivating the sensor and (ii) adapting sampling rate of the sensor.

In a further embodiment, the signal further comprises information about a time-period of usage of the health device, wherein the method further comprises operating the sensor for the time duration in a first power mode based on the time-period of usage of the health device. Typically, the sensor of the wearable device can be activated as soon as it is detected that the health device is in use. However, in the current advantageous embodiment, a further power management can be achieved, by switching ON the sensor when the method determines that a usage time-period of the device is more than a time threshold. For instance, a typical asthma relieving device should relieve the patient of the unpleasant situation in first ten minutes after taking few puffs, such as two to three puffs, however, if the method determines that the asthma relieving device is being used again after the first ten minutes, the method can accordingly trigger the sensor of the wearable device to start measuring the breathing rate for a time duration, such as ten minutes. In another example, an oxygen concentrator, for instance works continuously and hence if the oxygen concentrator is used for more than a time threshold of usage, the method then can trigger a corresponding sensor to measure physiological parameter, such has breathing rate, for a time duration, such as 10 minutes.

In a further embodiment, the method generates an alert when the time-period of usage of the health device and the gathered physiological information deviates from a pre-defined correlation. In the current advantageous embodiment, for instance, the method determines that the device is being used already for four minutes and there is no corresponding improvement or the desired improvement observed based on the gathered physiological information, the method alerts the caregiver and/or the user of the health device. The alert may further include an advisory message. The alerts can be in form of display for the user to contact a doctor or can be direct trigger for the caregiver in form of a display, a text message, etc. Any of the known communication means can be utilized to alert the user/caregiver.

The device as defined in the claims can be a part of the health device. Thus, the health device can directly trigger the wearable device. Alternatively, the computer implemented method can be performed by an application, popularly termed as an app, installed on a wireless communication device, such as a mobile device. In this case, the app based on the detected health device can trigger the associated sensor in the wearable device accordingly. One can appreciate that various such combinations can be possible.

The examples provided above are only for illustrative purposes. Thus, similar examples can be envisaged for implantable devices.

BRIEF DESCRIPTION OF THE DRAWINGS

Examples of the invention will now be described in detail with reference to the accompanying drawings, in which:

FIG. 2 shows a Table 1 stored in a memory including rules associated with the health devices, according to the embodiment of the invention;

FIG. 3 shows the synchronous data gathering from a sensor in the wearable during the use of the health device, according to the embodiment of the invention.

FIG. 4 shows an alternative embodiment in which the method is executed by a wireless communication device, according to an embodiment of the invention;

DETAILED DESCRIPTION OF THE EMBODIMENTS

Figure 1:
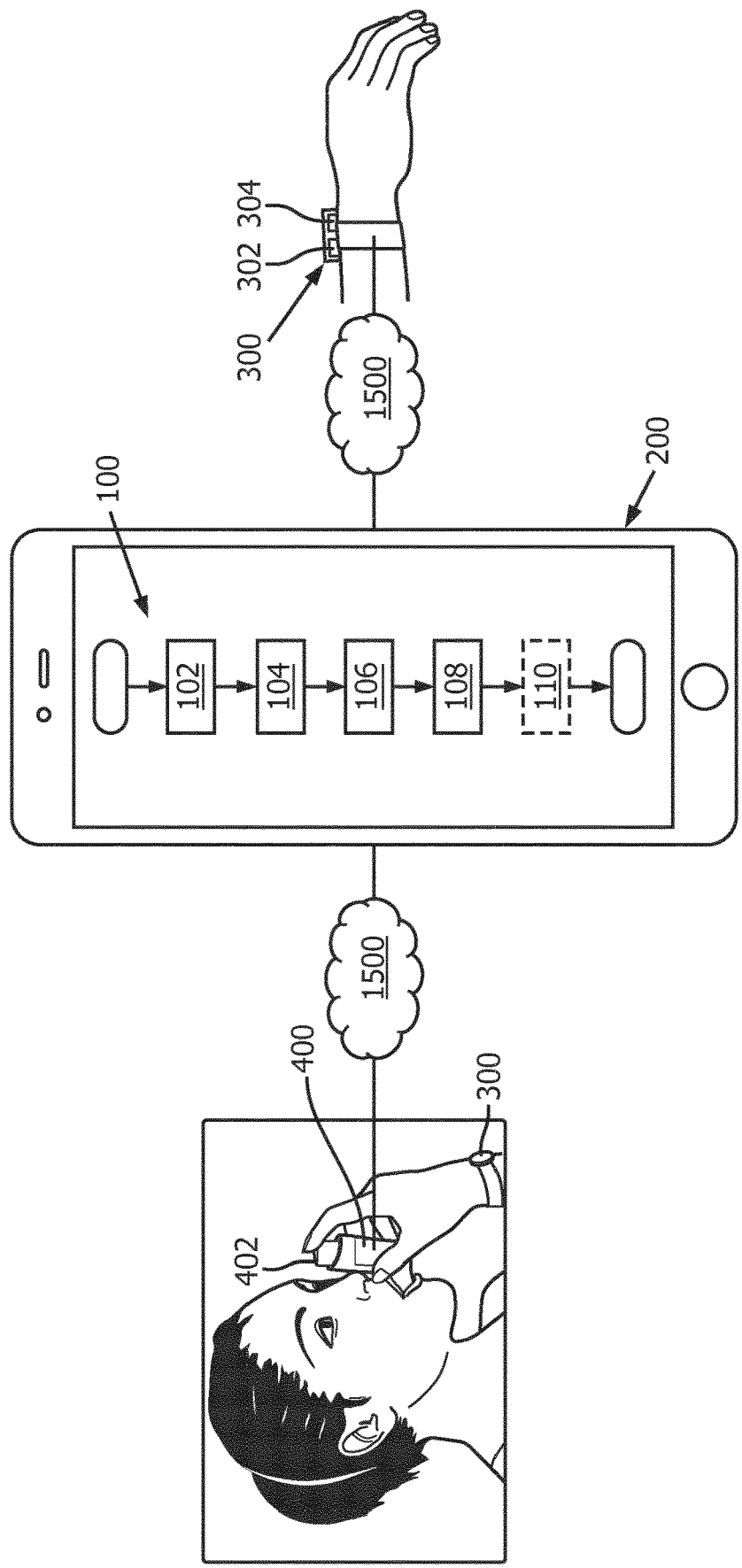
FIG. 1 shows a method executed by a wireless communication device for managing power of a wearable device, according to an embodiment of the invention.

FIG. 1 shows a method 100 executed by a wireless communication device 200 for managing power of a wearable device 300. An example of the wireless communication device 200 can be a smart phone, such as an iPhone®. In the current embodiment, the method can be in form of an application (app) that can be installed on the device 200. The health device 400 and wearable device 300 can be pre-registered with the app running on the wireless communication device 200.

In an alternate embodiment, the functionality of the wireless communication device 200 can be replaced by a standalone device that wirelessly communicates with the health device 400 and the wearable device 300. In yet another embodiment, the wearable device 300 can directly interact with the health device 400 or health devices without any intermediary device. It may be appreciated by a skilled person that the processing capabilities will then reside in the health device 400 that will trigger the wearable device 300. The devices 200, 300 and 400 interact over the wireless network 1500, such as Internet. In yet another embodiment, the health device 400 and the wearable device 300 can interact via a cloud network architecture.

In the current example, a health device 400 is an asthma relieving device, also known as an inhaler, herein after referred to as the inhaler 400. The inhaler 400 is typically positioned at the mouth such that the user can actuate by pressing the cartilage 402 containing the medicament, which causes subsequent release of the medicament in the mouth that is further inhaled by the user. During the period of the treatment, the device remains in the active state (or in use state) and treats an Asthma attack of the user. Further, the wearable device 300 can be a wrist worn device 300 with inbuilt physiological sensors, such as a breathing rate sensor 302, a heart rate sensor 304, a SpO₂ sensor (not shown), and the like.

The method at step 102, receives a signal from the device 400. The signal is indicative of whether a health device 400 which is configured to treat the health condition of the user is in use. In other words, the activation of the inhaler 400 by the user is signaled. In the current embodiment, the signal is received from the device 400 via the device 200.

Furthermore, the signal, indicates a type of health device. This is particular useful; when the user has multiple health devices. In this case, the signal will contain the information about type of the device, such as if the device 400 in use is an inhaler, or a pain relieving device, or an oxygen concentrator, or a CPAP device, etc. Essentially, the signal clearly identifies the health device 400. In an embodiment, a table (not shown in the figures) containing the unique identifiers identifying each health device can be stored and once the incoming signal containing a unique identifier is received from a health device, a comparison of the received vs stored information can be performed to identify the type of the health device. In the current embodiment, the identified device is the inhaler. In addition to the type of health device, the signal may optionally further indicate a time-period for which the health device 400 is already in use.

At step 104, a sensor is selected, based on the type of identified health device 400, from the plurality of sensors, such as 302, 304, etc. A table, such as Table 1, can store rules, which indicate which sensor needs to be activated/operated based on the type of the health device 400. In the current case, the breathing rate sensor 302 corresponding to the inhaler 400 is selected. As it can be seen in Table 1 that more than one health parameter/physiological parameter can be useful, when inhaler 400 is in use. Thus, more than one sensor corresponding to the health device 400 can be also be selected as well. For instance, for the inhaler 400, a heart rate sensor, a breathing rate sensor and a SpO₂ sensor can be selected to provide corresponding physiological information. In an embodiment, all the sensors that can provide such an information related to inhaler 400 can be activated based on a pre-defined condition, such as all at once, in a series with a time gap, etc. In the advantageous embodiment, a look up table, such as table 1 of FIG. 2 is stored in the memory (not shown) of the device 200. It may be appreciated by a person skilled in the art the selection of the sensor, such as sensor 302 is required when there are multiple sensors are available. It may be the case the wearable device 300 includes only one sensor, such as sensor 302, and is automatically triggered upon when the device 400 is in use.

At step 106, the method then operates the sensor 302 in a first power mode for a time duration. In an embodiment, the time duration is pre-defined. For instance, Table 1 indicates a time duration for which the sensor 302 must be operated in the first power mode. For instance, a breathing rate sensor can be operated for 10 minutes. The time can be pre-defined based on the understanding of how much information to gather in order to be useful for interpretation of a health status. This can be as well defined by the user, doctor, caregiver, etc.

When the sensor 302 is in the first power mode, the physiological information is gathered from the sensor 302 while the inhaler 400 is in use. Essentially, the physiological information is gathered synchronously. There are various ways in which synchronization can be achieved. For instance, the app to which the health device 400 and the wearable device 300 are connected can synchronize the receiving of the physiological information based on the start of the activation of the health device 400 and transfer of the data from the wearable device 300. Alternatively, an identifier can be used to synchronous receive a second signal from the sensor 302. When the health device is activated, it informs the app, which then signals a unique identifier to both devices (300, 400) and the data is tagged with the identifier. In this case, identifier and not time is used to link the data.

This is advantageous as the caregiver or the user can later also see the progress/statistics of the treatment during the use of the health device 400 based on the gathered data. Further, since the data gathering was synchronous, the information clearly indicates the information, such as rise/fall of the breathing rate in time during the use of the inhaler 400. In addition, based on the data gathered, the dosage of the inhaler 400 can be altered.

In an embodiment, the gathered synchronous data can be recorded in the wearable device 300 and later transferred on a remote device, where the analysis can be performed. It may be evident that the analysis can be performed on the wearable device 300 itself. Alternatively, the data can be simultaneously be transferred over the network 1500 to the device 200, where further statistics can be presented to the user via the device 200. One such statistics is provided in FIG. 3. As it can be seen, in start of the use of inhaler 400, the breathing rate was high, i.e. 25 breaths per minute, which later decreased to a normal breathing rate, which is between 12-18 breaths per minute.

At step 108, the sensor 302 is operated in a second power mode after the time duration has elapsed. In an embodiment, the sensor 302 is switched OFF after the time duration, i.e. 10 minutes following the above example, has elapsed. It may be appreciated the amount of physiological information that can provide insight on the effectiveness of the treatment is already captured and hence the sensor 302 need not be switched ON anymore. Thus, switching it OFF after the time duration has elapsed helps in better power management of the wearable device. Alternatively, the sampling rate of the sensor can be minimized, which also helps in saving power of the wearable device 300.

At step 110, optionally, if the time period of the usage of the device 400 and the physiological parameter information do not satisfy a pre-defined correlation than an alert can be further generated for a caregiver. This can also help in timely intervention by a caregiver, the user and a doctor.

FIG. 4 shows an alternative embodiment in which the method 100 is executed. In the current embodiment, the health device is a pain relieving device 500, advantageously, a phototherapy device 500 including one or more light sources 806 (FIG. 4a). The wearable device 300 in this case measures stress upon activation of a stress sensor 402. The stress sensor 402 can be a heart rate sensor 402a or a Galvanic Skin Response sensor 402b, wherein the stress can be further derived based on the heart rate and/or skin responses. Derivation of the stress based on heart rate and/or GSR responses is already well known in the state of the art and thus any of such method can be used to derive stress.

Similar to the last embodiment, the sensor 402a and/or 402b in the wearable device 300 is activated upon detection of the use of the pain relieving device 500 and based on the rule (in Table 1) associated with the pain relieving device 500. Further, the sensor 402a and/or the sensor 402b will be operated in a first power mode and a second power mode based on the rule defined in the Table 1.

Figure 5:
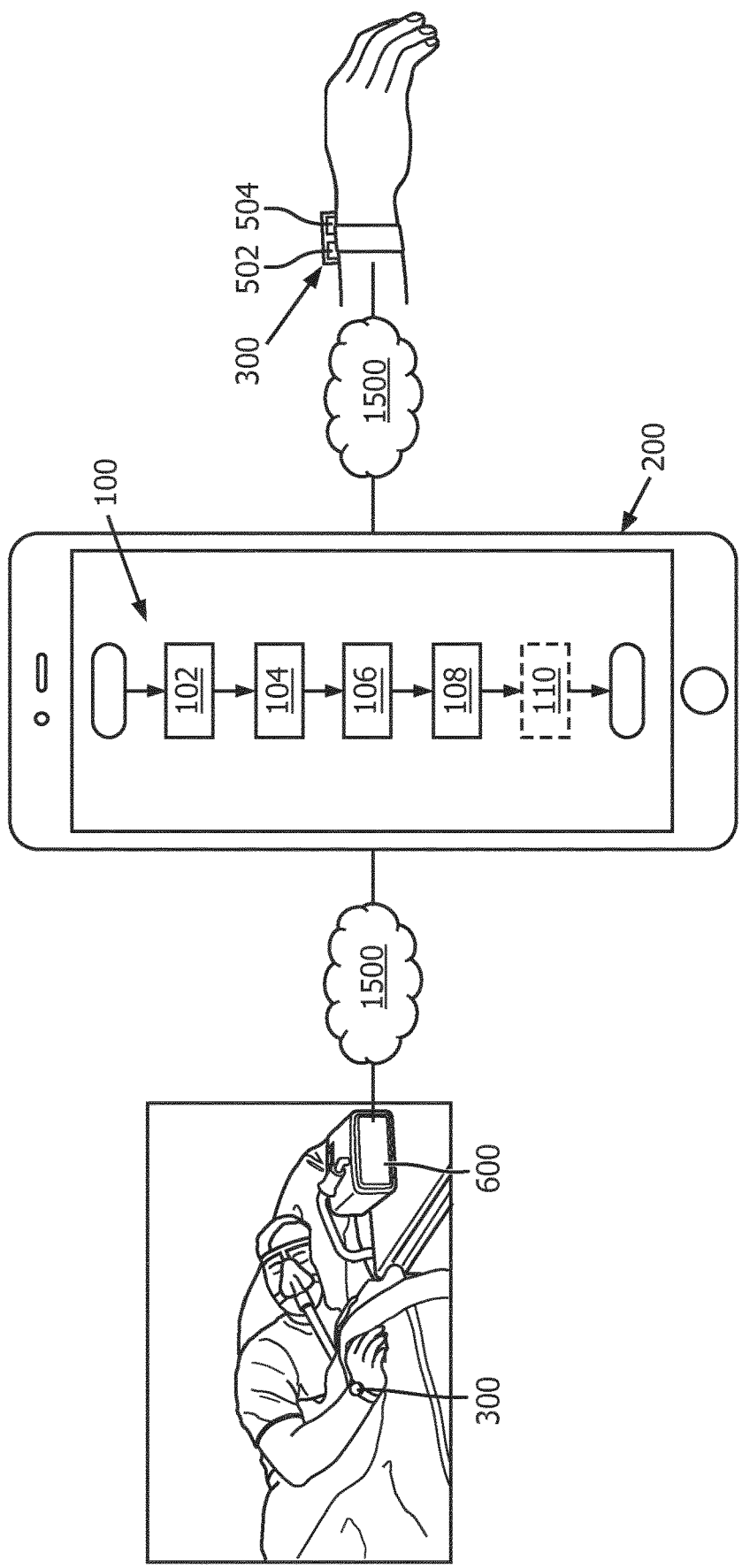
FIG. 5 shows a yet another embodiment in which the method is executed by a wireless communication device, according to an embodiment of the invention.

Similarly, yet another implementation (as depicted in FIG. 5) could be in form of Continuous positive airway pressure (CPAP) device 600 (a health device) and the wearable device 300. Similarly one or more associated sensors 502/504 can be activated and operated in one of the two modes based on the rule defined in the Table 1.

As it can be appreciated that the embodiments in FIG. 4 and FIG. 5 are explained with respect to the device 500/600 and device 300 interacting with the device 200 to execute the method 100. In an alternate embodiment, the functionality of the wireless communication device 200 can be replaced by a standalone device that wirelessly communicates with the health device 500/600 and the wearable device 300. In yet another embodiment, the wearable device 300 can directly interact with the health device 500 and/or health device 600 without any intermediary device. It may be appreciated by a skilled person that the processing capabilities will then reside in the health device 500/600 that will trigger the wearable device 300. The devices 200, 300 and 400/600 interact over the wireless network 1500, such as Internet. In yet another embodiment, the health device 500 and/or health device 600 and the wearable device 300 can interact via a cloud network architecture.

Figure 6:
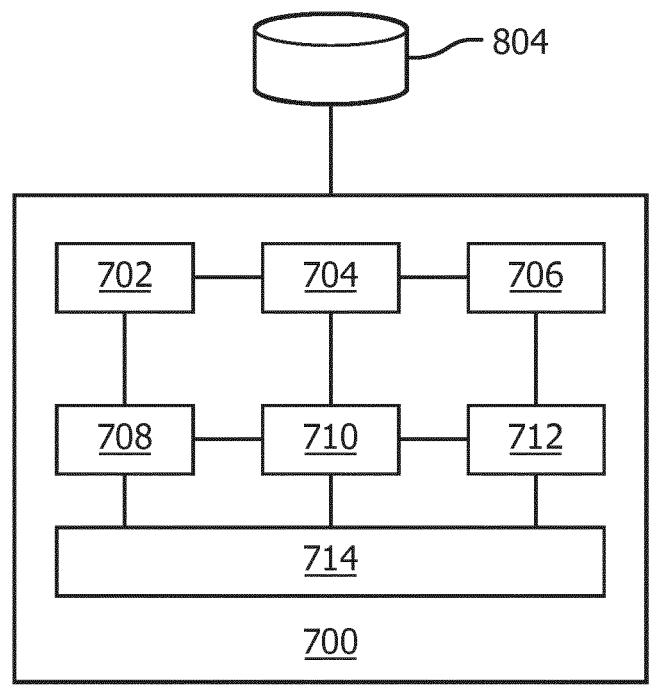
FIG. 6 shows a device according to an embodiment of the invention.

FIG. 6 shows a device 700 according to an embodiment of the invention. The device 700 includes a receiving module 702, a selecting module 704, an operating module 706, a recording module 708, an analysis module 710, an alert module 712 and a processing module 714. Modules of the device 700 are in electronic communication with each other. Device 700 can be a standalone device or can be part of a wireless communication device, such as wireless communication device 200

The receiving module 702 receives a signal being indicative of whether a health device, such device as health device 400 (or 500 or 600) in FIG. 1, which is configured to treat a health condition of the user when it is in use. The receiving module 702 receives the signal from a transceiver (not shown), which provides information about the status, such as in use, and type of the health device 400. The transceiver can be inbuilt in the health device 400. In an embodiment, the receiving module 702 can be a transceiver (not shown).

The selecting module 704 interacts with the memory 804 to recognize the health device 400. A look up table containing unique identifiers identifying each health device can be also stored in the memory 804. The selecting module 704 compares the received "type" information with the stored information to recognize the type of the health device 400. As explained earlier, the received signal from the health device 400 includes a unique identifier identifying the health device 400 in use and the selecting module 704 compares the received unique identifier with the stored unique identifiers to recognize/identify the health device 400 in use.

Thereafter, the selecting module 704 based on type of the identified health device generates and transmits a selecting signal for selecting and triggering a sensor of a wearable device 300 accordingly. Pre-defined rules can be stored that clearly indicate which sensor to be selected based on the type of the health device. Further rules can also indicate the power regime to be followed, such as for the duration that the selected senor has to be switched ON, duty cycle, sampling rate, etc. This is further detailed in step 104 of method 100 explained in FIG. 1. The look up table, such as table 1, can be stored in a memory, such as the memory 804. The memory 804 can be inbuilt in the health device 400. Alternatively, the memory 804 can be remote from the health device 400 can be accessed over a network, such as network 1500. The memory module 804 can be as well the memory of a wireless communication device, such as device 200. In some embodiments, the memory 804 can be part of the device 700. The operating module 706, once the sensor has been selected, then transmits an operating signal to the selected sensor of the wearable device to perform steps 106 and 108 of the method 100 explained in FIG. 1.

The recording module 708 furthermore saves the gathered physiological information in the memory 804. The analysis module 710 further performs analysis on the recorded information in order to provide an output signal that can be indicative of a patterns, such as in FIG. 3, and presented on a display (not shown) of the device 200. Further, the device 700 includes the alert module 712 to provide an alert signal to a caregiver, user, doctor, when the gathered information vis-a-vis time of usage of the health device 400 deviates from a pre-defined correlation. The alerts can be provided on a display of the wearable device 300 or on the display of wireless communication device 200 or on the display of the health device 400/500/600. Alternate way of alerting such as audio, tactile can be also envisaged.

Figure 6A:
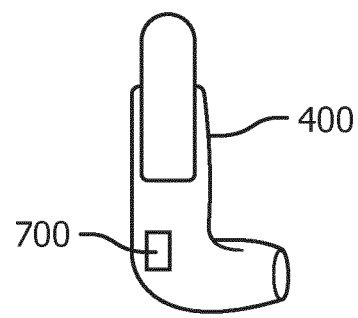
FIG. 6a shows the device included in a health device, according to an embodiment of the invention.

In an alternate embodiment (FIG. 6a), the device 700 is inbuilt in the health device, such as inhaler 400.

In an embodiment, the device 700 is a hardware device for executing software that can be stored in a memory. In some embodiments, the modules, such as the receiving module 702, the selecting module 704, the operating module 706, the recording module 708, the analysis module 710, and the alert module 712 may be implemented as a software running on the processing unit 714. These modules may be stored as software instructions in the memory, such as memory 804, of the device 700 and the processing unit 714 in communication with the modules executes the software instructions stored therein. In some embodiments, the device 700 may be implemented in hardware, or in a combination of software and hardware. The processor module 714, i.e. also may be referred to as a processing unit 714, can be virtually any custom made or commercially available processor, a central processing unit (CPU), a digital signal processor (DSP), or an auxiliary processor among several processors associated with a computer, and the processor may be a semiconductor based microprocessor (in the form of a microchip) or a microprocessor.

The memory 804 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory may incorporate electronic, magnetic, optical, and/or other types of storage media. Note that the memory can have a distributed architecture, where various components are situated remote from one another, but can be accessed by the processor.

The software in the memory may include one or more separate programs, each of which comprises an ordered listing of executable instructions for implementing logical functions. The software in the memory for example may include one or more of a suitable operating system (O/S), compiler, source code, and one or more applications in accordance with exemplary embodiments.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for power management of a user device comprising a plurality of sensors, the user device being wearable by or implantable in a user having a health condition, wherein each sensor is configured to provide corresponding physiological information of the user, and to be operated in a first power mode and a second power mode, wherein the sensor consumes less power in the second power mode than in the first power mode, the method comprising:
   receiving a signal from a health device that has been activated to provide treatment of the health condition of the user, wherein the signal indicates that the health device is in use by the user and a type of the health device;
   selecting at least one sensor from the plurality of the sensors of the user device based on the type of the health device in use;
   gathering physiological information of the user during the treatment of the health condition for a time duration following activation of the health device using the selected at least one sensor;
   operating the selected at least one sensor in the first power mode for the time duration to gather the physiological information of the user, and operating the selected at least one sensor in the second power mode after the time duration ends; and
   measuring effectiveness of the treatment provided by the health device with regard to improving the health condition of the user based on the gathered physiological information during and after the time duration.

2. The method according to claim 1, wherein the physiological information comprises vital signs information and/or physiological state derived from the vital signs information.

3. The method according to claim 1, wherein the time duration is based on a time duration threshold.

4. The method according to claim 1, further comprising recording the physiological information during the time duration.

5. The method according to claim 1, wherein operating the selected at least one sensor in the second power mode comprises deactivating the selected at least one sensor.

6. The method according to claim 1, further comprising receiving information about a time-period of usage of the health device, wherein the time duration is based on the time-period of usage of the health device.

7. The method according to claim 6, further comprising generating an alert when the time-period of usage of the health device and the physiological information deviate from a pre-defined correlation.

8. The method according to claim 1, further comprising determining the time duration to gather the physiological information of the user based on the measured effectiveness of the treatment of the health condition by the health device.

9. The method according to claim 8, wherein measuring the effectiveness of the treatment comprises comparing the gathered physiological information with a pre-determined effectiveness threshold.

10. The method according to claim 1, wherein operating the selected at least one sensor in the second power mode comprises adapting a sampling rate of the selected at least one sensor.

11. The method of claim 1, wherein the received signal indicates that the health device comprises an inhaler, and wherein selecting the at least one sensor from the plurality of the sensors comprises selecting at least a breathing rate sensor, a heart rate sensor, and a $SpO_2$ sensor.

12. The method of claim 1, wherein the received signal indicates that the health device comprises a phototherapy device, and wherein selecting the at least one sensor from the plurality of the sensors comprises selecting at least a heart rate sensor and a Galvanic Skin Response sensor.

13. The method of claim 1, wherein the received signal indicates that the health device comprises a continuous positive airway pressure (CPAP) device, and wherein selecting the at least one sensor from the plurality of the sensors comprises selecting at least a breathing rate sensor and a $SpO_2$ sensor.

14. The method of claim 1, wherein the received signal indicates that the health device comprises an oxygen concentrator, and wherein selecting the at least one sensor from the plurality of the sensors comprises selecting at least a breathing rate sensor and a $SpO_2$ sensor.

15. A non-transitory computer readable medium that stores software instructions for power management of a user device comprising a plurality of sensors, the user device being wearable by or implantable in a user having a health condition, wherein each sensor is configured to provide corresponding physiological information of the user, and to operate in a first power mode and a second power mode, wherein the sensor consumes less power in the second power mode than in the first power mode, when executed by a processor, the software instructions cause the processor to perform steps comprising:
    receiving a signal from a health device that is activated to provide treatment of the health condition of the user, wherein the signal indicates that the health device is in use by the user and a type of the health device;
    selecting at least one sensor from the plurality of the sensors of the user device based on the type of the health device in use;
    causing physiological information of the user to be gathered during the treatment of the health condition for a time duration following the activation of the health device using the selected at least one sensor;
    operating the selected at least one sensor in the first power mode for the time duration to gather the physiological information of the user, and operating the selected at least one sensor in the second power mode after the time duration ends; and
    measuring effectiveness of the treatment provided by the health device with regard to improving the health condition of the user based on the gathered physiological information during and after the time duration.

16. The non-transitory computer readable medium according to claim 15, wherein the physiological information comprises vital signs information and/or physiological state derived from the vital signs information.

17. The non-transitory computer readable medium according to claim 15, wherein the time duration is based on a measure of the effectiveness of the treatment of the health condition by the health device, and wherein the measure of the effectiveness of the treatment is evaluated by comparing the gathered physiological information with a pre-determined effectiveness threshold.

* * * * *